United States Patent

Suzuki et al.

Patent Number: 4,724,269
Date of Patent: Feb. 9, 1988

[54] PROCESS FOR PRODUCING P-CHLOROBENZENES

[75] Inventors: Toshihiro Suzuki; Chizu Komatsu, both of Shizuoka, Japan

[73] Assignee: Ihara Chemical Industry Co., Ltd., Tokyo, Japan

[21] Appl. No.: 875,685

[22] Filed: Jun. 18, 1986

[51] Int. Cl.⁴ .............................................. C07C 17/12
[52] U.S. Cl. ..................... 570/208; 568/656
[58] Field of Search .................... 570/208, 207, 206; 568/656

[56] References Cited

U.S. PATENT DOCUMENTS 2,473,990  6/1946  Darragh .............................. 570/208

FOREIGN PATENT DOCUMENTS 112722   7/1984  European Pat. Off. ............ 570/208
118851   9/1984  European Pat. Off. ............ 570/208
0154236 11/1985  European Pat. Off. .
48943A   8/1983  Japan .................................. 568/656
2155009A 9/1985  United Kingdom ................ 570/206

Primary Examiner—Donald B. Moyer
Assistant Examiner—Joseph A. Boska
Attorney, Agent, or Firm—Oblon, Fisher, Spivak, McClelland & Maier

[57] ABSTRACT

A process for producing a p-chlorobenzene having the formula:

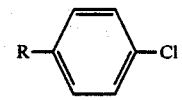

(I)

wherein R is a lower alkyl group, a lower alkoxy group or a halogen atom, which comprises chlorinating a benzene having the formula:

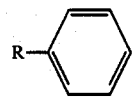

(II)

wherein R is as defined above, in a liquid phase in the presence of a catalyst, characterized in that the catalyst is a combination of an aliphatic alcohol having the formula:

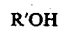

R'OH (III)

wherein R' is a lower alkyl group or a lower haloalkyl group, and a zeolite having a $SiO_2/Al_2O_3$ molar ratio of from 3 to 8 and a pore size of from 6 to 10 Å.

12 Claims, No Drawings

PROCESS FOR PRODUCING P-CHLOROBENZENES

The present invention relates to a process for producing a p-chlorobenzene such as p-chlorotoluene or p-dichlorobenzene which is useful as a starting material for the production of medicines and agricultural chemicals. More particularly, it relates to a process for producing a p-chlorobenzene such as p-chlorotoluene or p-dichlorobenzene with a high selectivity by chlorinating a benzene with use of a novel catalyst.

Chlorobenzenes are useful as starting materials for medicines and agricultural chemicals. Particularly, there are strong demands for p-chlorobenzenes such as p-chlorotoluene and p-dichlorobenzene among them. Accordingly, there have been various studies to improve the selectivity for p-chlorobenzenes.

Namely, as a process for producing p-chlorobenzenes by chlorinating benzenes in a liquid phase in the presence of a catalyst, there have been proposed, for instance, a method wherein toluene is chlorinated by using a catalyst comprising a Lewis acid and sulfur or selenium to obtain p-chlorotoluene with a selectivity of from 45 to 52%, a method wherein toluene is chlorinated by using a catalyst comprising a Lewis acid and thianthrene to obtain p-chlorotoluene with a selectivity of from 55 to 60% (U.S. Pat. No. 4,031,147), a method wherein toluene is chlorinated by using a catalyst comprising a Lewis acid and a phenoxathiin compound to obtain p-chlorotoluene with a selectivity of from 52 to 60% (U.S. Pat. No. 4,444,983), a method wherein chlorobenzene is chlorinated by using iron sulfide as a catalyst to obtain p-dichlorobenzene with a selectivity of from 60 to 70% (U.K. Pat. No. 1,476,398), and a method wherein chlorobenzene is chlorinated by using selenium or a selenium compound as a catalyst to obtain p-dichlorobenzene with a selectivity as high as about 72% (Japanese Examined Patent Publication No. 34010/1975). Further, as an improvement over these conventional methods, the present inventors have earlier proposed a method wherein toluene is chlorinated by using L-type zeolite as a catalyst to obtain p-chlorotoluene with a selectivity of about 65% (EP No. 112,722A1), or a method wherein chlorobenzene is chlorinated by using L-type zeolite as a catalyst to obtain p-dichlorobenzene with a selectivity of about 86% (EP No. 118,851A1).

However, none of these methods provides a sufficient selectivity for p-chlorobenzenes, and is not necessarily satisfactory as a process for producing p-chlorobenzenes. Under the circumstances, it has been desired to develop a method which is capable of producing p-chlorobenzenes with a better selectivity and less production of by-products.

Accordingly, it is an ojbect of the present invention to provide a process for producing p-chlorobenzenes with a high selectivity by the chlorination of substituted benzenes in a liquid phase in the presence of a catalyst.

The present inventors have conducted extensive researches to overcome the above-mentioned drawbacks inherent to the conventional methods and to develop a process capable of producing p-chlorobenzenes with a high selectivity. As a result, they have found that the object can be attained by using a combination of a certain selected zeolite and a certain selected aliphatic alcohol, as a catalyst. The present invention has been accomplished on the basis of this discovery.

Namely, the present invention provides a process for producing a p-chlorobenzene having the formula:

 (I)

wherein R is a lower alkyl group, a lower alkoxy group or a halogen atom, which comprises chlorinating a benzene having the formula:

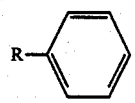 (II)

wherein R is as defined above, in a liquid phase in the presence of a catalyst, characterized in that the catalyst is a combination of an aliphatic alcohol having the formula:

$$R'OH \quad (III)$$

wherein R' is a lower alkyl group or a lower haloalkyl group, and a zeolite having a $SiO_2/Al_2O_3$ molar ratio of from 3 to 8 and a pore size of from 6 to 10 Å.

Now, the present invention will be described in further detail with reference to the preferred embodiments.

The feature of the present invention is to use a combination of a certain selected zeolite and a certain selected aliphatic alcohol, as a catalyst, as a means to solve the conventional problems.

Namely, in the process of the present invention, it is essential to use, as a catalyst, a combination of a zeolite having a $SiO_2/Al_2O_3$ molar ratio of from 3 to 8 and a pore size of from 6 to 10 Å, and an aliphatic alcohol having the formula III.

The zeolite which satisfies such conditions, includes L-type zeolite which is a crystalline aluminosilicate having a $SiO_2/Al_2O_3$ molar ratio of from 4 to 8 and a pore size of from 7 to 10 Å, and Y-type zeolite having a $SiO_2/Al_2O_3$ molar ratio of from 3 to 7 and a pore size of from 6 to 9 Å. It is also possible to employ a synthetic zerolite having the same X-ray diffraction spectrum as the above-mentioned L-type or Y-type zeolite. Further, the ion exchangeable cations contained in such zeolite are usually sodium or potassium, but may further include other cations. As such cations, there may be mentioned metal ions or protons belonging to Group IA, Group IIA, Group IIIA, Group IVA or Group VA of the periodic table. These cations may be of the same type or of two or more different types.

If a zeolite having a $SiO_2/Al_2O_3$ molar ratio or a pore size outside the above ranges, i.e. a zeolite other than L-type zeolite and Y-type zeolite, is used as the zeolite, the selectivity for p-chlorobenzenes will be substantially reduced, and it is thereby impossible to achieve the object of the present invention.

The aliphatic alcohol of the formula III used as a catalyst in the process of the present invention, may be a $C_2$ or $C_3$ alkanol or haloalkanol, such as ethanol, propanol, 2-chloroethanol, 2,2-dichloroethanol, 2,2,2-trichloroethanol, 2-bromoethanol, 2-fluoroethanol, 2,2,2-trifluoroethanol, 3-chloro-1-propanol, 2,3-dichloro-1-propanol, 3,3,2-tetrafluoro-1-propanol, 3,3,3,2-pentafluoro-1-propanol, or 1,1,1,3,3,3-hexafluoro-2-propanol. Particularly preferred among them are 2-chloroethanol, 2,2-dichloroethanol, 3-chloro-1-propanol and 2,3-dichloro-1-propanol. The aliphatic alcohol is used in an amount of at least 1% by weight relative to the above-mentioned zeolite, and preferably in an amount of from 3 to 30% by weight relative to the zeolite.

If an alcohol other than the aliphatic alcohol of the formula III, such as 6-chloro-1-hexanol, 2-chlorocyclohexanol or phenol is used, the object of the present invention can hardly be accomplished (see Comparative Examples 2, 3 and 4 given hereinafter).

In the present invention, a combination of the above-mentioned zeolite and the above-mentioned aliphatic alcohol is employed. This combination may be made by mixing the above-mentioned zeolite and the above-mentioned aliphatic alcohol prior to the chlorination reaction, or by adding the aliphatic alcohol and the zeolite simultaneously to the reaction system at the time of the chlorination reaction.

The preparation of the catalyst prior to the chlorination may be conducted, for instance, by suspending the above zeolite in a solvent, adding the aliphatic alcohol thereto, distilling off the solvent and any excess amount of the aliphatic alcohol and then drying the residue under reduced pressure. In this case, the zeolite may directly be added to the aliphatic alcohol without using a solvent, followed by distilling off the excess amount of the alcohol.

Whereas, in the case where the catalyst is prepared at the time of the reaction, a predetermined amount of the zeolite is suspended in the starting material benzene charged in the chlorination apparatus, and then the aliphatic alcohol is added thereto, and the mixture is stirred at a temperature of not higher than the boiling point, preferably from room temperature to 100° C., more preferably from 40° to 90° C., for about 30 minutes. Then, a chlorinating agent is added, and the chlorination reaction is conducted.

The benzene of the formula II used as the starting material in the process of the present invention, includes compounds of the formula II wherein the substituent R is a straight or branched lower alkyl such as methyl, ethyl, n-propyl, i-propyl, n-butyl, i-butyl, t-butyl, or s-butyl or lower alkoxy group such as methoxy, ethoxy or n-propoxy or a halogen atom such as a fluorine atom, a chlorine atom or a bromine atom. It is particularly preferred to employ a compound wherein R is a methyl group or a chlorine atom, whereby the effects of the present invention are most remarkable.

To conduct the chlorination of the benzene of the formula II by the process of the present invention, the catalyst i.e. the combination of the aliphatic alcohol and the zeolite, is added usually in an amount of from 0.01 to 10 g, preferably from 0.1 to 7 g, per mol of the benzene of the formula II, and then a chlorinating agent is introduced to conduct the reaction in a liquid phase at a temperature of not higher than the boiling point of the mixture, preferably from room temperature to 100° C., more preferably from 40° to 90° C., under stirring. For this reaction, a solvent may be employed, as the case requires. However, no solvent is usually employed.

The chlorinating agent may be an agent which is commonly used for the chlorination of an aromatic ring. Preferably, chlorine or sulfuryl chloride is employed. Particularly preferred is chlorine. Such a chlorinating agent may be employed by diluting it with an inert gas such as nitrogen, as the case requires.

The chlorination reaction may be conducted under reduced pressure or under elevated pressure, but is usually conducted under atmospheric pressure.

According to the process of the present invention, it is possible to selectively and efficiently chlorinate the p-position of the benzene of the formula II while supressing the chlorination at the o-position, and to minimize the formation of by-products such as side chain-chlorinated products or polychlorinated products, whereby a highly useful p-chlorobenzene of the formula I can be obtained in a high selectivity as compared with the conventional methods, for instance, in a selectivity of 75% for p-chlorotoluene, or in a selectivity of 92% for p-dichlorobenzene.

Further, according to the process of the present invention, in a case where p-dichlorobenzene is to be produced from chlorobenzene as the starting material, it is possible to advantageously conduct the production of chlorobenzene from benzene and the step of chlorinating the chlorobenzene to p-dichlorobenzene, continuously in the same reactor.

Furthermore, according to the process of the present invention, the operation of the reaction and the subsequent after-treatment are simple, and it is possible to reuse the catalyst. Thus, the process of the present invention is suitable as an industrial process for the production of p-chlorobenzenes.

Now, the present invention will be described in further detail with reference to Examples. However, it should be understood that the present invention is by no means restricted by these specific Examples.

EXAMPLE 1

Into a 100 ml reaction flask equipped with a condenser, a thermometer, a stirrer and a gas supply tube, 2.5 g of L-type zeolite (TSZ-506, tradename, manufactured by Toyo Soda Manufacturing Co., Ltd.) and 46.1 g (0.5 mol) of toluene were introduced, and 0.5 g of 2-chloroethanol was added thereto. The mixture was maintained at 70° C., and stirred for 30 minutes while supplying nitrogen gas. Then, chlorine gas was supplied at a rate of 0.125 mol/hr for 3.6 hours to conduct the reaction while maintaining the reaction temperature at 70° C. After the completion of the reaction, the reaction product thereby obtained, was analyzed by gas chromatography, whereby it was found that the conversion of toluene was 87.6%, the production ratio of o-chlorotoluene/p-chlorotoluene (hereinafter referred to simply as "o/p ratio") was 0.298, and the selectivity for p-chlorotoluene relative to the total amount of the reaction product was 75%.

EXAMPLE 2

The reaction as in Example 1 was repeated by using the same catalyst again, whereby the conversion of toluene was 88.2% and the o/p ratio was 0.299.

EXAMPLES 3 to 6 and COMPARATIVE EXAMPLES 1 to 4

The halogenation was conducted at 70° C. in the same manner as in Example 1 except that various alcohols were used instead of 2-chloroethanol. The results are shown in Table 1.

For the purpose of comparison, the results obtained in the case where L-type zeolite was used alone as the sole catalyst, are also given.

TABLE 1

| | Alcohols | Conversion (%) | o/p ratio | Selectivity for p-chlorobenzene (%) |
|---|---|---|---|---|
| Example 3 | 2,3-Dichloro-1-propanol | 89.4 | 0.387 | 70 |
| Example 4 | 2,2-Dichloroethanol | 89.6 | 0.342 | 73 |
| Example 5 | 3-Chloro-1-propanol | 87.4 | 0.341 | 69 |
| Example 6 | Propanol | 88.5 | 0.453 | 67 |
| Comparative Example 1 | None | 87.9 | 0.5 | 63 |
| Comparative Example 2 | 6-Chloro-1-hexanol | 87.7 | 0.522 | 60 |
| Comparative Example 3 | 2-Chlorocyclohexanol | 82.6 | 0.440 | 61 |
| Comparative Example 4 | Phenol | 85.0 | 0.510 | 62 |

EXAMPLES 7 to 9

The chlorination was conducted in the same manner as in Example 1 excpet that the reaction temperature was changed. The results are shown in Table 2.

TABLE 2

| Example | Aliphatic alcohols | Temp. | Conversion (%) | o/p ratio | Selectivity for p-chlorobenzene |
|---|---|---|---|---|---|
| 7 | 2-Chloroethanol | 50° C. | 89.8 | 0.317 | 69.3 |
| 8 | 2-Chloroethanol | 65° C. | 89.6 | 0.301 | 74.3 |
| 9 | 2-Chloroethanol | 90° C. | 89.5 | 0.350 | 71.3 |

EXAMPLES 10 to 13 and COMPARATIVE EXAMPLES 5 to 8

The chlorination was conducted in the same manner as in Example 1 except that toluene was changed to other benzenes. For the purpose of comparison, the results obtained in the case where L-type zeolite was used alone as the sole catalyst, are also given.

TABLE 3

| | Benzene | Conversion (%) | o/p ratio | Selectivity for p-chlorobenzene (%) |
|---|---|---|---|---|
| Example 10 | Chlorobenzene | 74.7 | 0.076 | 93 |
| Comparative Example 5 | Chlorobenzene | 73.5 | 0.12 | 87 |
| Example 11 | Cumene | 81.5 | 0.215 | 77 |
| Comparative Example 6 | Cumene | 81.0 | 0.26 | 72 |
| Example 12 | Anisole | 89.5 | 0.194 | 78 |
| Comparative Example 7 | Anisole | 88.7 | 0.21 | 75 |
| Example 13 | t-Butylbenzene | 84.1 | 0.031 | 91 |
| Comparative Example 8 | t-Butylbenzene | 83.5 | 0.06 | 82 |

What is claimed is:

1. A process for producing a p-chlorobenzene having the formula:

(I)

wherein R is a lower alkyl group, a lower alkoxy group or a halogen atom, which comprises chlorinating a benzene having the formula:

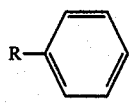
(II)

wherein R is as defined above, in a liquid phase in the presence of a catalyst, characterized in that the catalyst is a combination of an aliphatic alcohol having the formula:

R'OH (III)

wherein R' is a lower haloalkyl group, and a zeolite having a SiO$_2$/Al$_2$O$_3$ molar ratio of from 3 to 8 and a pore size of from 6 to 10 Å.

2. The process according to claim 1, wherein the aliphatic alcohol is a C$_2$ or C$_3$ haloalkanol.

3. The process according to claim 1, wherein the aliphatic alcohol is 2-chloroethanol.

4. The process according to claim 1, wherein the aliphatic alcohol is 2,2-dichloroethanol.

5. The process according to claim 1, wherein the aliphatic alcohol is 3-chloro-1-propanol or 2,3-dichloro-1-propanol.

6. The process according to claim 1, wherein the aliphatic alcohol is used in an amount of at least 1% by weight relative to the zeolite.

7. The process according to claim 1, wherein the aliphatic alcohol is used in an amount of from 3 to 30% by weight relative to the zeolite.

8. The process according to claim 1, wherein the catalyst is used in an amount of from 0.01 to 10 g per mol of the benzene of the formula II.

9. The process according to claim 1, wherein the catalyst is used in an amount of from 0.1 to 7 g per mol of the benzene of the formula II.

10. The process according to claim 1, wherein the chlorination is conducted at a temperature of not higher than the boiling point of the reaction mixture.

11. The process according to claim 1, wherein the zeolite is L-type zeolite.

12. The process according to claim 1, wherein the aliphatic alcohol is selected from the group consisting of 2-chloroethanol, 2,2-dichloroethanol, 3-chloro-1-propanol and 2,3-dichloro-1-propanol.

* * * * *